(12) United States Patent
Minato

(10) Patent No.: US 9,046,533 B2
(45) Date of Patent: Jun. 2, 2015

(54) METHOD AND SYSTEM FOR SYNCHRONOUSLY DRIVING LIGHT-DISPERSING ELEMENTS, AND DETECTOR FOR CHROMATOGRAPH

(75) Inventor: Hiroyuki Minato, Kyoto (JP)

(73) Assignee: SHIMADZU CORPORATION, Kyoto-shi (JP)

(*) Notice: Subject to any disclaimer, the term of this patent is extended or adjusted under 35 U.S.C. 154(b) by 425 days.

(21) Appl. No.: 13/478,301

(22) Filed: May 23, 2012

(65) Prior Publication Data

US 2012/0307237 A1    Dec. 6, 2012

(30) Foreign Application Priority Data

May 30, 2011  (JP) ................................. 2011-120025

(51) Int. Cl.
*G01J 3/00*  (2006.01)
*G01N 30/74*  (2006.01)

(52) U.S. Cl.
CPC ...................................... *G01N 30/74* (2013.01)

(58) Field of Classification Search
CPC ...................................... H02P 8/10; H02P 8/40
See application file for complete search history.

(56) References Cited

U.S. PATENT DOCUMENTS 3,869,656 A * 3/1975 Kennedy et al. ............... 318/696
2004/0046956 A1 * 3/2004 Gould et al. .................. 356/333

FOREIGN PATENT DOCUMENTS

JP           03-144347 A    6/1991
JP      2000-314661 A    11/2000

OTHER PUBLICATIONS

Japanese Office Action dated Sep. 2, 2014, issued in corresponding Japanese Application No. 2011-120025, w/ English translation (5 pages).

* cited by examiner

*Primary Examiner* — Tri T Ton
*Assistant Examiner* — Willie Merrell, II
(74) *Attorney, Agent, or Firm* — Westerman, Hattori, Daniels & Adrian, LLP

(57) ABSTRACT

Provided is a system for synchronously driving light-dispersing elements capable of synchronously and sequentially changing an excitation-light wavelength and a fluorescence wavelength at high speeds. The system includes: a first light-dispersing unit having a first light-dispersing element and a first pulse motor; a second light-dispersing unit having a second light-dispersing element and a second pulse motor; a memory section for storing light-dispersing element information relating to a change in the wavelength of the monochromatic light and the dynamic characteristics information of the pulse motors; a drive condition setting section for allowing an operator to set synchronous drive conditions; a pulse transmission pattern creator; and a pulse transmitter.

6 Claims, 5 Drawing Sheets

TRAPEZOIDAL DRIVE

"S"-SHAPE DRIVE

CONSTANT-SPEED DRIVE

METHOD AND SYSTEM FOR SYNCHRONOUSLY DRIVING LIGHT-DISPERSING ELEMENTS, AND DETECTOR FOR CHROMATOGRAPH

TECHNICAL FIELD

The present invention relates to a method and system for synchronously driving light-dispersing elements, and more specifically to such a method and system suitable for driving light-dispersing elements in a detector section of a chromatograph. The present invention also relates to a detector for a chromatograph.

BACKGROUND ART

A spectrofluorometric method is commonly used as a detection method for chromatograph systems. Although the spectrofluorometric method is only available for the detection of fluorescent substances, this technique is broadly used, because it is capable of an analysis with dramatically high sensitivity as compared to an optical absorption method, which utilizes absorption of light by a substance. FIG. 1 is a schematic configuration diagram of a spectrofluorometric detector for performing a spectrofluorometric method.

In this spectrofluorometric detector 1, light generated by a light source (e.g. Xenon lamp) having a broad continuous spectrum ranging from the ultraviolet region through the near infrared region is introduced into an excitation-light dispersing device 11, which turns the light into a monochromatic light of a specific excitation-light wavelength by a diffraction grating 11a driven by a motor. This monochromatic light is cast as excitation light into a sample cell 12 containing a sample solution 13. Upon being irradiated with the excitation light, the sample solution 13 emits a faint fluorescence, which is introduced into a fluorescence dispersing device 14. In this device, only a fluorescence of a specific wavelength is extracted by a diffraction grating 14a and sent to a photomultiplier tube 15. This tube 15 produces a current signal corresponding to the intensity of the incident light. The current signal is converted into a voltage signal by a current-to-voltage (I/V) converter 16 and further into a digital value by an analogue-to-digital (A/D) converter 17, to be ultimately sent to a data processor 18 as detection data. By processing and analyzing the detection data, the data processor 18 calculates a quantitative value of a specific component in the sample solution 13.

Normally, in a spectrofluorometric method, a three-dimensional fluorescent spectrum having the three axes of excitation-light wavelength, fluorescence wavelength and fluorescence intensity is obtained by repeating the measurement in which either the excitation-light wavelength or fluorescence wavelength is sequentially changed while the other wavelength is fixed.

This method requires a considerable length of time to search for peaks since the excitation-light wavelength and the fluorescence wavelength must be independently and sequentially changed to obtain a fluorescent spectrum. To address this problem, a method for efficiently searching for peaks has been proposed in Patent Document 1. To improve the peak-searching efficiency, this method utilizes the characteristic fact that a large number of peaks on a fluorescent spectrum obtained by sequentially changing the excitation-light wavelength and the fluorescence wavelength have their fluorescence wavelengths being longer than their excitation-light wavelengths by 20 nm to 140 nm. According to this method, a fluorescent spectrum is obtained by simultaneously changing the excitation-light wavelength and the fluorescence wavelength while controlling these wavelengths so that the fluorescence wavelength is always longer than the excitation-light wavelength by 20 to 140 nm.

In this method, a rough yet efficient search of a peak is initially performed by simultaneously changing the excitation-light wavelength and the fluorescence wavelength. After a peak is found, the excitation-light wavelength and the fluorescence wavelength are independently changed to obtain detailed information. Accordingly, the measurement requires less time than in the case of the conventional spectrofluorometric method in which each of the excitation-light and fluorescence wavelengths is independently changed over the entire range of the measurement wavelength.

To measure a fluorescent spectrum by this method, a preliminary measurement or the like is previously performed to collect, for each of the excitation-light and fluorescence dispersing devices, information relating to the number of pulses to be sent to the pulse motor for driving the light-dispersing element and the change in the wavelength of the monochromatic light produced by the light-dispersing element. Using this information, it is possible to determine the numbers of pulses to be respectively sent to the excitation-light pulse motor and the fluorescence pulse motor so as to concurrently change the excitation-light wavelength and the fluorescence wavelength under given spectrofluorometric measurement conditions (the measurement-beginning wavelength, the measurement-ending wavelength, and the wavelength-changing interval).

BACKGROUND ART DOCUMENT

Patent Document

Patent Document 1: JP-A 3-144347

SUMMARY OF THE INVENTION

Problem to be Solved by the Invention

Various methods for driving common pulse motors are known. FIGS. 2A-2C show examples: a constant-speed drive, which uses a constant drive speed, as well as a trapezoidal drive and an "S"-shape drive, which are advantageous for shortening the drive time. Any of these three methods is typically used to synchronously change the wavelength of the excitation light and that of the fluorescence. However, when the trapezoidal or "S"-shape drive is used to simultaneously drive the excitation-light pulse motor and the fluorescence pulse motor while maintaining a constant difference between the excitation-light wavelength and the fluorescence wavelength, it is difficult to maintain the constant difference during the driving operation, because each pulse motor requires a different number of pulses to be sent. As a result, the excitation-light wavelength and the fluorescence wavelength obtained by the synchronous drive become significantly different from the true values, so that a process for determining the true values of the excitation-light wavelength and the fluorescence wavelength must be subsequently performed, or if such a process already exists, additional steps must be included in the process. Using a constant-speed drive or making the trapezoidal or S-shape drive approximate to the constant-speed drive to reduce the error takes time to change the wavelengths when obtaining a fluorescent spectrum. This imposes restrictions on the measurement. For example, when this method is used in the detector section of a chromatograph system, the measurement cannot be performed while the sample is flowing; the sample must be statically held in a cell during the measurement.

The problem to be solved by the present invention is to provide a method and system for synchronously driving light-dispersing elements as well as a detector for a chromatograph, in which the excitation-light wavelength and the fluorescence wavelength can be synchronously and sequentially changed at high speeds.

Means for Solving the Problems

A method for synchronously driving light-dispersing elements according to the present invention aimed at solving the aforementioned problem is a method for driving a first light-dispersing element and a second light-receiving element in a light-dispersing device including: a first light-dispersing unit having the first light-dispersing element and a first pulse motor for driving the first light-dispersing element; a second light-dispersing unit having the second light-dispersing element and a second pulse motor for driving the second light-dispersing element; and a pulse transmitter for transmitting a first pulse number of pulses to the first pulse motor and a second pulse number of pulses to the second pulse motor, the first pulse number of pulses being necessary for sequentially changing, at predetermined intervals, a wavelength of monochromatic light produced by the first light-dispersing device, and the second pulse number of pulses being necessary for sequentially changing, at predetermined intervals, a wavelength of monochromatic light produced by the second light-dispersing device, and the method including the steps of:

determining a transmission rate of the first pulse number of pulses based on a pulse rate within a start/stop region or slew range of the first pulse motor;

calculating a first pulse transmission time from the first pulse number and the transmission rate of the first pulse number of pulses; and transmitting the second pulse number of pulses to the second pulse motor within the first pulse transmission time.

If the second pulse number is greater than the first pulse number, and therefore, the transmission rate of the pulses to the second pulse motor must be higher than that of the pulses to the first pulse motor, or if the first and second pulse motors have different characteristics of the start/stop region and/or slew range, it is possible that the transmission rate of the second pulse number of pulses to the second pulse motor deviates from the start/stop region or slew range of the second pulse motor, causing the second pulse motor so step out.

To address this problem, the method according to one preferable mode of the present invention includes the steps of checking whether the transmission rate of the second pulse number of pulses sent to the second pulse motor is within the start/stop region or slew range of the second pulse motor, and reducing the transmission rate of the second pulse number of pulses while increasing the transmission rate of the other portion of the second pulse number of pulses to be sent within the first pulse transmission time if the transmission rate of the second pulse number of pulses is out of the aforementioned region or range.

By this method, both the first and second pulse motors can be assuredly driven at high speeds, in a synchronized fashion, and at pulse rates within the start/stop region or slew range.

A system for synchronously driving light-dispersing elements according to the present invention aimed at solving the aforementioned problem is a system including: a first light-dispersing unit having a first light-dispersing element and a first pulse motor for driving the first light-dispersing element; and a second light-dispersing unit having a second light-dispersing element and a second pulse motor for driving the second light-dispersing element, the system being capable of synchronously driving the first light-dispersing element and the second light-receiving element by transmitting a first pulse number of pulses to the first pulse motor and a second pulse number of pulses to the second pulse motor, the first pulse number of pulses being necessary for sequentially changing, at predetermined intervals, a wavelength of monochromatic light produced by the first light-dispersing device, and the second pulse number of pulses being necessary for sequentially changing, at predetermined intervals, a wavelength of monochromatic light produced by the second light-dispersing device, and the system further including:

a) a memory section for storing first light-dispersing element information relating to the number of pulses to be sent to the first pulse motor and a change in the wavelength of the monochromatic light produced by the first light-dispersing element, second light-dispersing element information relating to the number of pulses to be sent to the second pulse motor and a change in the wavelength of the monochromatic light produced by the second light-dispersing element, dynamic characteristics information of the first pulse motor relating to a start/stop region and slew range of the first pulse motor, and dynamic characteristics information of the second pulse motor relating to a start/stop region and slew range of the second pulse motor;

b) a drive condition setting section for allowing an operator to set, as synchronous drive conditions, a change-beginning wavelength, a change-ending wavelength and a wavelength-change interval of the monochromatic lights produced by the first light-dispersing element and the second light-dispersing element;

c) a pulse transmission pattern creator for creating a first pulse transmission pattern for transmitting the first pulse number of pulses within a first pulse transmission time, based on the first light-dispersing element information, the pulse rate within the start/stop region or slew range of the first pulse motor and the synchronous drive conditions, and for creating a second pulse transmission pattern for transmitting the second pulse number of pulses within the first pulse transmission time; and d) a pulse transmitter for transmitting pulses to the first pulse motor and the second pulse motor, based on the first pulse transmission pattern and the second pulse transmission pattern.

In one preferable mode of the system according to the present invention, the pulse transmission pattern creator checks whether the transmission rate of the second pulse number of pulses sent to the second pulse motor is within the start/stop region or slew range of the second pulse motor, and reduces the transmission rate of the second pulse number of pulses while increasing the transmission rate of the other portion of the second pulse number of pulses to be sent within the first pulse transmission time if the transmission rate of the second pulse number of pulses is out of the aforementioned region or range.

By this system, both the first and second pulse motors can be assuredly driven at high speeds, in a synchronized fashion, and at pulse rates within the respective start/stop region or slew range.

The system for synchronously driving light-dispersing elements according to the present invention is suitable for driving light-dispersing elements of a detector for a chromatograph using a spectrofluorometric method.

Effect of the Invention

By the method and system for synchronously driving light-dispersing elements according to the present invention, the first and second light-dispersing elements can be simultaneously driven at higher speeds than in the conventional cases. When a system for synchronously driving light-dispersing elements according to the present invention is used as a system for driving light-dispersing elements in a detector for a chromatograph, a fluorescent spectrum can be obtained in a short period of time by synchronously driving the light-dispersing devices. Therefore, it is possible to perform the measurement of a sample in the flowing state.

BEST MODE FOR CARRYING OUT THE INVENTION

Figure 1:
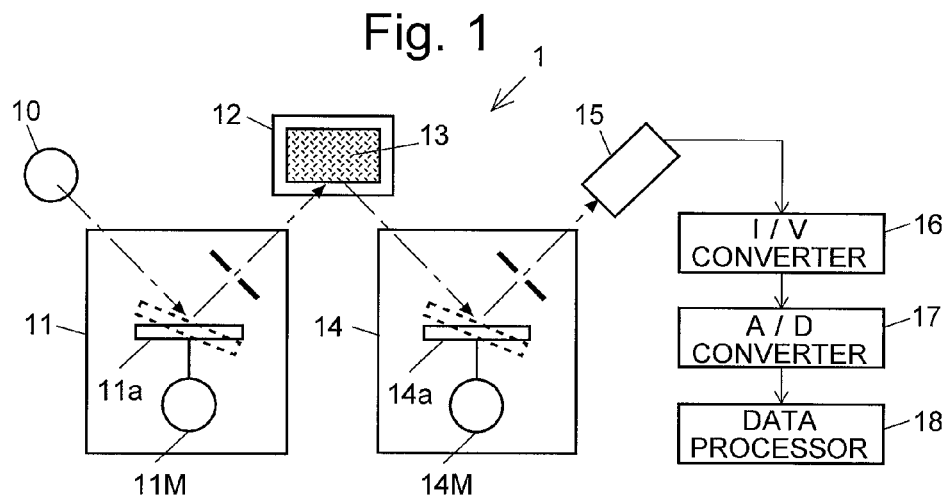
FIG. 1 is a diagram illustrating the schematic configuration of a spectrofluorometric detector.
Figure 3:
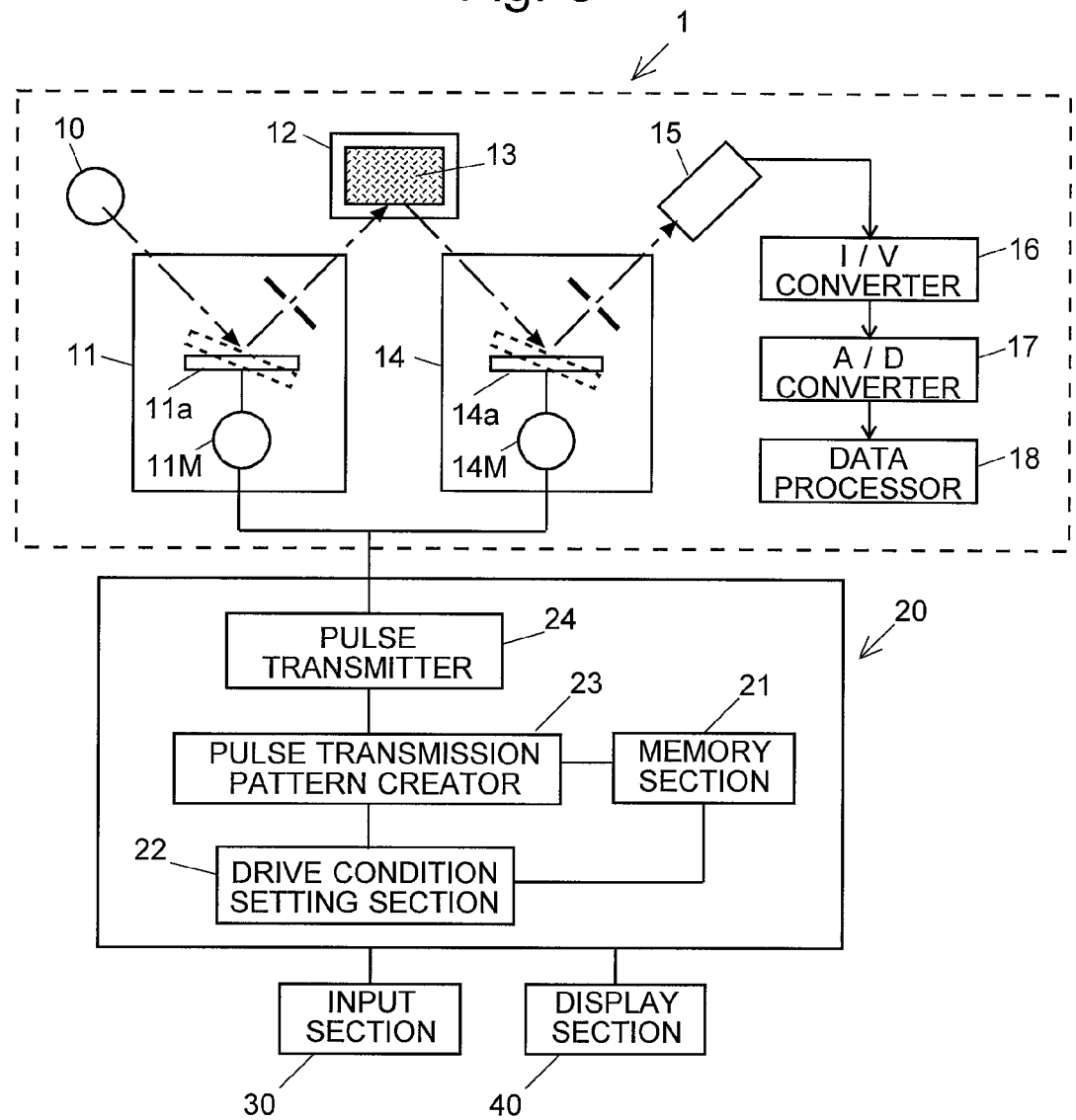
FIG. 3 is a diagram illustrating one embodiment in which a system for synchronously driving light-dispersing elements is applied to a detector of a chromatograph.

One embodiment in which the present invention is applied to a system for driving light-dispersing elements in a detector (spectrofluorometric detector) for a chromatograph is hereinafter described by means of FIG. 3. The spectrofluorometric detector 1 shown in the upper part of FIG. 3 is the same as shown in FIG. 1. Therefore, the same numerals are used for this detector and no description will be made for it.

The synchronous drive system 20 for light-dispersing elements according to the present embodiment has a memory section 21, a drive condition setting section 22, a pulse transmission pattern creator 23 and a pulse transmitter 24. An input unit 30 for allowing an operator to enter synchronous drive conditions and other information and a display unit 40 for showing drive conditions and other information are connected to the synchronous drive system 20. The pulse transmitter 24 of the synchronous drive system 20 is connected to an excitation-light pulse motor 11M and a fluorescence pulse motor 14M.

Stored in the memory section 21 is information relating to the excitation-light pulse motor 11M and the excitation-light diffraction grating 11a as well as information relating to the fluorescence pulse motor 14M and the fluorescence diffraction grating 14a. These kinds of information are hereinafter collectively referred to as the "light-dispersing device information."

The information relating to the excitation-light pulse motor 11M includes an excitation-light pulse number, dynamic characteristics (which include pulse-rate information of the start/stop region and the slew range) and so on. The information relating to the excitation-light diffraction grating 11a includes the wavelength of monochromatic light to be produced by the excitation-light diffraction grating 11a. The information relating to the fluorescence pulse motor 14M and the fluorescence diffraction grating 14a also includes similar kinds of information.

Also stored in the memory section 21 are the synchronous drive conditions. Synchronous drive conditions include the change-start wavelength, the change-end wavelength and the wavelength-change interval of monochromatic lights produced by the excitation-light diffraction grating 11a and the fluorescence diffraction grating 14a. These parameters are set by the drive condition setting section 22. More specifically, the drive condition setting section 22 shows a synchronous drive condition input screen on the display unit 40, allowing the operator to set synchronous drive conditions on this screen by using the input unit 30. The synchronous drive conditions set by the operator are transmitted to and stored in the memory section 21.

The pulse transmission pattern creator 23 reads the synchronous drive conditions and the light-dispersing device information from the memory section 21 and creates pulse transmission patterns to be sent to the excitation-light pulse motor 11M and the fluorescence pulse motor 14M. The created pulse transmission patterns are sent to the pulse transmitter 24. A specific method for creating the pulse transmission patterns to be sent to the excitation-light pulse motor 11M and the fluorescence pulse motor 14M will be specifically described later. The pulse transmission patterns should be created so as to synchronously drive the excitation-light dispersing device 11 and the fluorescence dispersing device 14 at high speeds without causing the excitation-light pulse motor 11M and the fluorescence pulse motor 14M to lose steps.

The pulse transmitter 24 sends the received pulse transmission patterns to the excitation-light dispersing device 11 and the fluorescence dispersing device 14. Based on these patterns, the excitation-light dispersing device 11 and the fluorescence dispersing device 14 of the spectrofluorometric detector 1 synchronously drive the excitation-light pulse motor 11M and the fluorescence pulse motor 14M at high speeds.

A method for synchronously driving light-dispersing elements according to the present embodiment is hereinafter described.

Figure 2A:
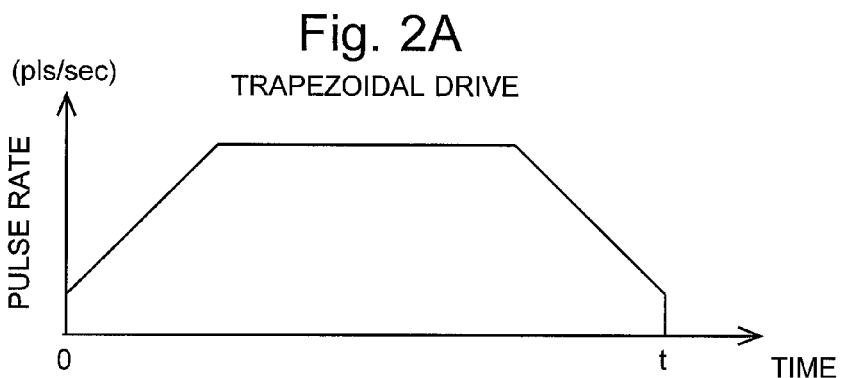
FIGS. 2A-2C are graphs illustrating the dynamic characteristics of a commonly used pulse motor.
Figure 2B:
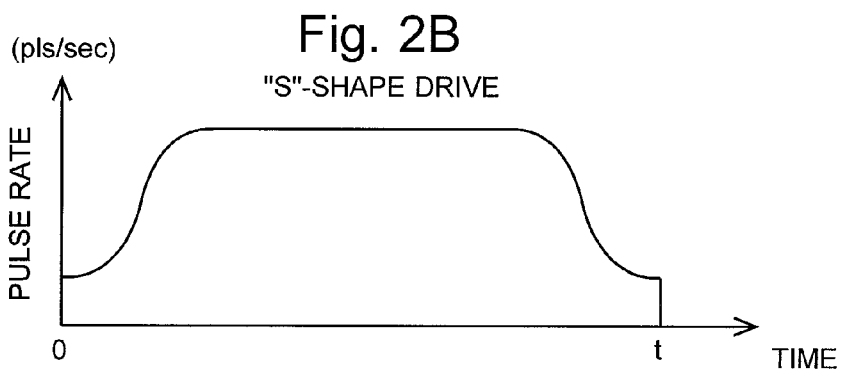
Figure 2C:
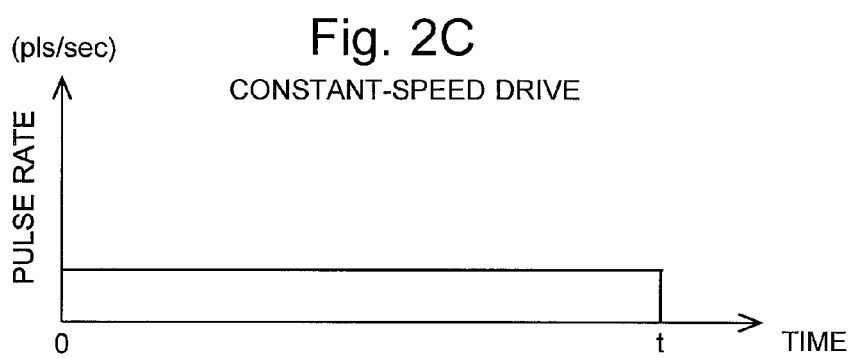

In the present embodiment, the detector for a chromatograph shown in FIG. 3 is controlled so that the wavelength of the monochromatic light produced by the excitation-light diffraction grating 11a changes from A nm to B nm in steps of 1 nm, while the wavelength of the monochromatic light produced by the fluorescence diffraction grating 14a changes from A+α nm to B+α nm in steps of 1 nm, where α is the difference between the fluorescence wavelength to be measured and the excitation-light wavelength to be cast on a sample and should be appropriately set according to the purpose of the measurement. This wavelength difference α is maintained at a constant value during the synchronous driving of the light-dispersing elements. Both the excitation-light pulse motor 11M and the fluorescence pulse motor 14M have a trapezoidal drive characteristic as shown in FIG. 2A.

A preliminary experiment or the like is conducted to obtain information relating to the excitation-light pulse motor 11M and the excitation-light diffraction grating 11a as well as information relating to the fluorescence pulse motor 14M and the fluorescence diffraction grating 14a. These kinds of information are hereinafter collectively referred to as the "light-dispersing device information."

The information relating to the excitation-light pulse motor 11M includes an excitation-light pulse number, dynamic characteristics information (which include pulse rate information of the start/stop region and the slew range) and so on. The information relating to the excitation-light diffraction grating 11a includes the wavelength of monochromatic light to be produced by the excitation-light diffraction grating 11a. The information relating to the fluorescence pulse motor 14M and the fluorescence diffraction grating 14a also includes similar kinds of information.

The range of the wavelength-change interval to be referenced in Step S42 (which will be described later) is also previously set.

Figure 4:
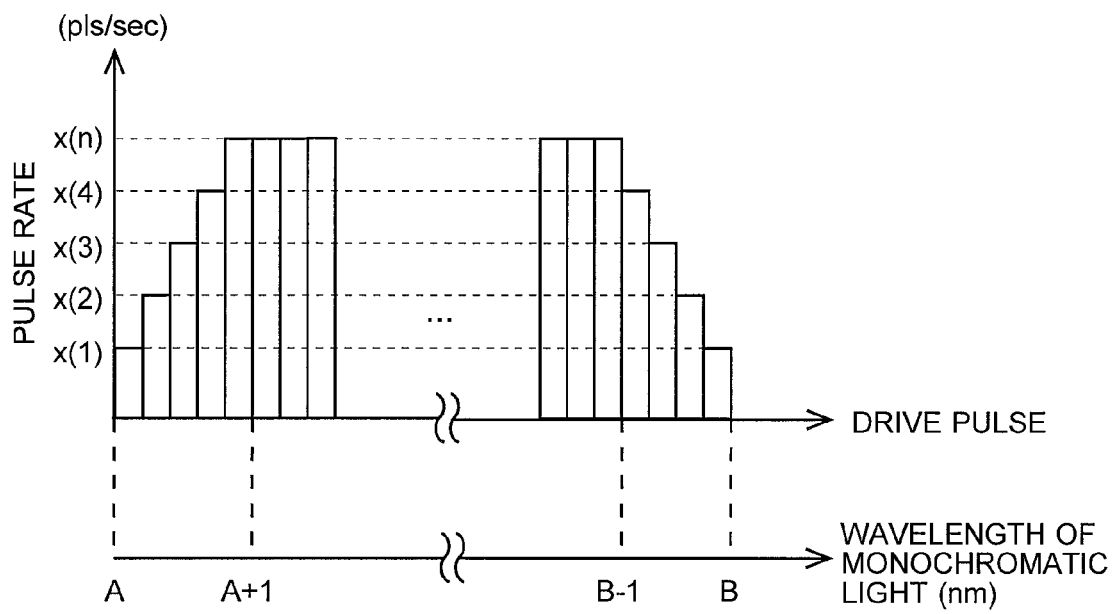
FIG. 4 is a diagram illustrating a method for creating an excitation-light pulse transmission pattern.

Based on the information relating to the excitation-light diffraction grating 11a, the excitation-light pulse number to be sequentially sent to the excitation-light pulse motor 11M is determined so as to change the wavelength of the monochromatic light produced by the excitation-light diffraction grating 11a from A nm to B nm in steps of 1 nm. Subsequently, based on the dynamic characteristics information of the excitation-light pulse motor 11M, an excitation-light pulse transmission pattern to be used for sending each pulse at the highest pulse rate within the start/stop region or slew range is created. Since the pulse motors used in the present embodiment have a trapezoidal drive characteristic, the excitation-light pulse transmission pattern also has a trapezoidal shape, as shown in FIG. 4. In this figure, x(1) is an appropriate pulse rate within the start/stop region, and x(2), x(3), x(4) and x(n) are appropriate pulse rates within the slew range. After the excitation-light pulse transmission pattern is created, the excitation-light pulse transmission time for sequentially transmitting the excitation-light pulse number of pulses to the excitation-light diffraction grating 11a is determined.

Figure 5:
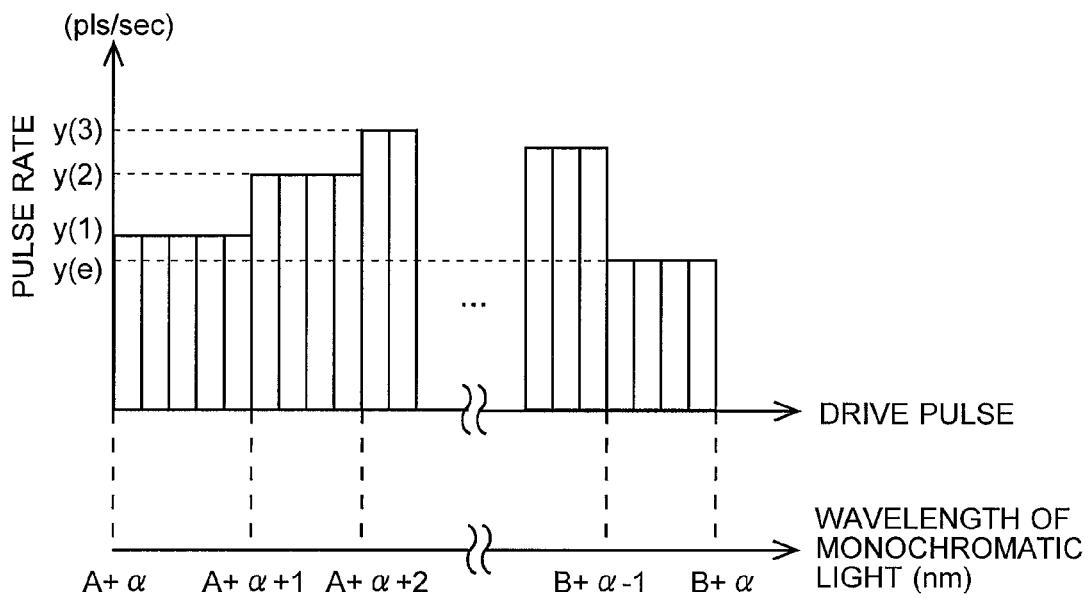
FIG. 5 is a diagram illustrating a method for creating a fluorescence pulse transmission pattern.

Subsequently, based on the information relating to the fluorescence diffraction grating 14a, the fluorescence pulse number to be sent to the fluorescence pulse motor 14M is sequentially determined so as to change the wavelength of monochromatic light produced by the fluorescence diffraction grating 14a from A+α nm to B+α in steps of 1 nm. Then, the excitation-light pulse transmission time is divided by the fluorescence pulse number to determine the pulse rates y(1), y(2), y(3), . . . , y(e) to be sent to the fluorescence pulse motor 14M. Thus, the fluorescence pulse transmission pattern is created (FIG. 5).

Based on the excitation-light pulse transmission pattern (FIG. 4) and the florescence pulse transmission pattern (FIG. 5) prepared by the previously described procedure, the pulse transmitter 24 sends pulses to the excitation-light pulse motor 11M and the fluorescence pulse motor 14M, respectively. As a result, the excitation-light diffraction grating 11a and the fluorescence diffraction grating 14a are synchronously driven at high speeds.

In the previously described method, the fluorescence pulse transmission pattern is created without taking into account information relating to the dynamic characteristics of the fluorescence pulse motor 14M. Therefore, for example, if the fluorescence pulse number is greater than the excitation-light pulse number, or if the excitation-light pulse motor 11M and the fluorescence pulse motor 14M have different characteristics of the start/stop region and/or slew range, it is possible that the pulse rate of the fluorescence pulse transmission pattern exceeds the upper limit of the start/stop region or slew range of the fluorescence pulse motor 14M, causing this motor to step out. To prevent this situation, it is desirable to add the following procedure to check the pulse rate of the fluorescence pulse transmission pattern and modify this pattern as needed.

Figure 6:
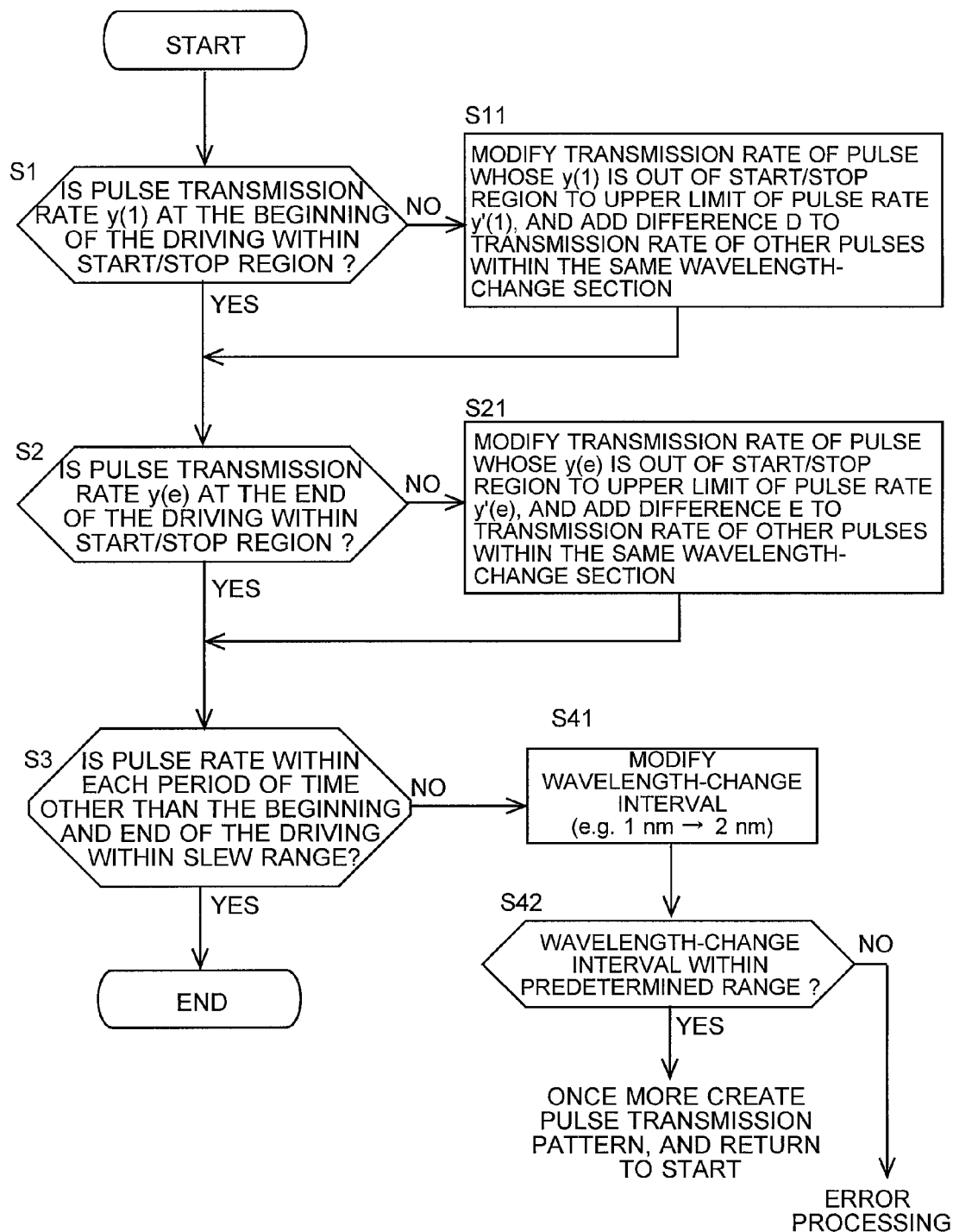
FIG. 6 is a flowchart illustrating a procedure for modifying the fluorescence pulse transmission pattern.
Figure 7A:
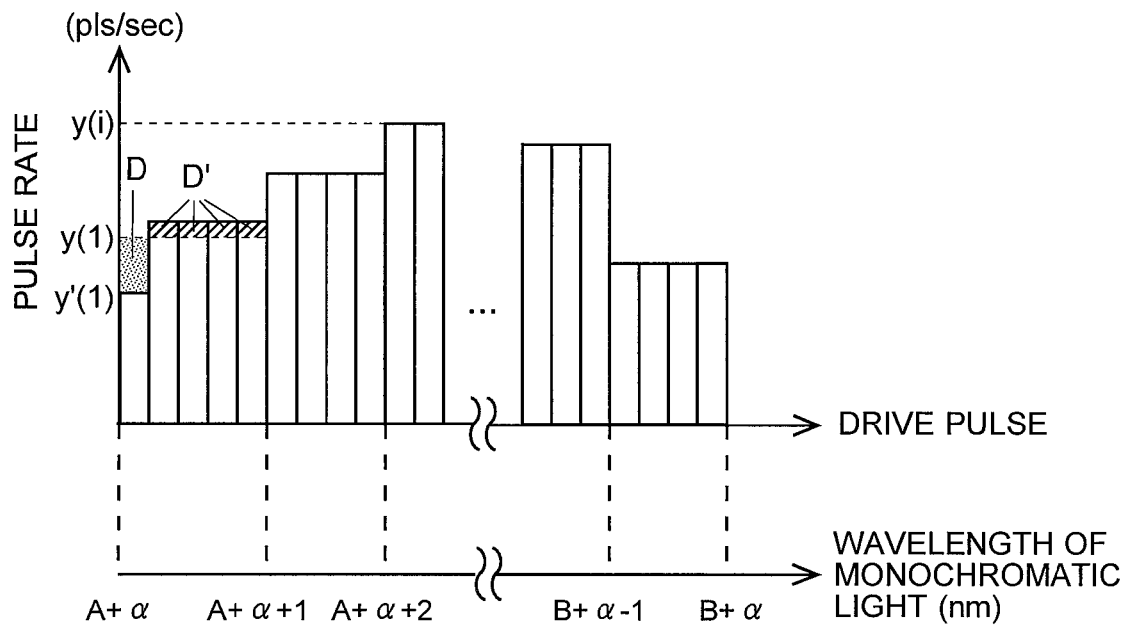
FIGS. 7A and 7B are diagrams illustrating a method for modifying the fluorescence pulse transmission pattern.
Figure 7B:
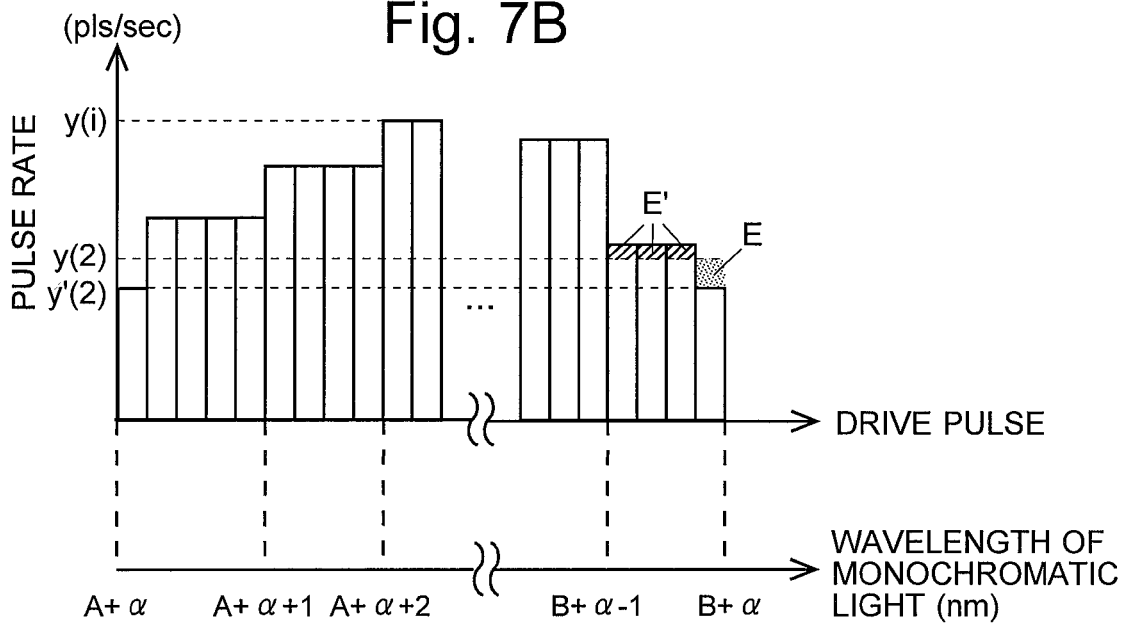

A procedure and method for modifying the pulse transmission pattern will be described by means of FIGS. 6, 7A and 7B. Initially, whether the pulse rate y(1) at the beginning of the driving of the pulse motor is within the start/stop region is checked (Step S1). If there is any pulse whose pulse rate y(1) exceeds the upper limit of the start/stop region, the pulse rate of that pulse is modified from y(1) to the level y'(1) which equals the upper limit of the start/stop region. The difference D resulting from this modification is added to the other pulses to be sent within the period of changing the wavelength of the monochromatic light from A+α nm to A+α+1 nm (Step S11). FIG. 7A shows an example in which the pulse rate y(1) of the first pulse exceeds the upper limit of the start/stop region. In this example, the pulse rate at which the first pulse is sent is modified to y'(1). The difference D resulting from this modification is balanced by adding D' to each of the other four pulses being sent within the same pulse transmission time. Thus, the pulse transmission time is adjusted to the same length as before.

Next, the pulse rate of the pulse transmission pattern at the end of the driving is also modified as needed by performing Steps S2 and S21 similar to Steps S1 and S11. FIG. 7B shows an example in which the pulse rate y(e) for the last pulse exceeds the upper limit of the start/stop region. In this example, the pulse rate at which the last pulse is sent is modified to y'(e). The difference E resulting from this modification is balanced by adding E' to each of the other three pulses being sent within the same pulse transmission time. Thus, the pulse transmission time is adjusted to the same length as before.

As the end, whether the pulse rate within each period of time other than the beginning and end of the driving is within the slew range of the pulse motor is checked (Step S3). If any pulse is found to be outside the slew range, the wavelength-change interval is modified (Step S41).

In the case of modifying the wavelength-change interval, whether the wavelength-change interval after the modification is within a predetermined range is checked (Step S42). If the interval after the modification is within the predetermined range, the excitation-light pulse transmission pattern and the fluorescence pulse transmission pattern are once more created by the previously described procedure.

Conversely, if the wavelength-change interval after the modification is out of the predetermined range, an error processing is performed, such as displaying a message urging the operator to once more set the synchronous drive conditions.

The previous embodiments are mere examples of the present invention and can be appropriately changed or modified within the spirit of the present invention. For example, in the previous embodiment, the excitation-light pulse transmission pattern was created earlier, after which the fluorescence pulse number of pulses necessary for changing the fluorescence wavelength by a predetermined wavelength-change interval were transmitted within the excitation-light pulse transmission time for transmitting the excitation-light pulse number of pulses necessary for changing the excitation-light wavelength by the predetermined wavelength-change interval. However, the synchronous driving of the excitation-light dispersing element and the fluorescence dispersing element can be achieved even if the fluorescence pulse transmission pattern is created earlier.

In the previous embodiments, the synchronous driving was performed in such a manner as to maintain the difference in wavelength between the monochromatic excitation-light produced by the excitation-light dispersing element and the monochromatic fluorescence light produced by the fluorescence dispersing element. However, the present invention is also applicable in a case where the wavelength-change interval for the monochromatic light produced by the first light-dispersing element is set to be different from the wavelength-change interval for the monochromatic light produced by the second light-dispersing element.

EXPLANATION OF NUMERALS

1 ... Spectrofluorometric Detector
10 ... Light Source
11 ... Excitation-Light Dispersing Device
11a ... Excitation-Light Diffraction Grating
11M ... Excitation-Light Pulse Motor
12 ... Sample Cell
13 ... Sample Solution
14 ... Fluorescence Dispersing Device
14a ... Fluorescence Diffraction Grating
15 ... Photomultiplier Tube
16 ... Current-to-Voltage (I/V) Converter
17 ... Analogue-to-Digital (A/D) Converter
18 ... Data Processor
20 ... Synchronous Drive System
21 ... Memory Section
22 ... Drive Condition Setting Section
23 ... Pulse Transmission Pattern Creator
24 ... Pulse Transmitter
30 ... Input Unit
40 ... Display Unit

The invention claimed is:

1. A method for synchronously driving light-dispersing elements for driving a first light-dispersing element and a second light-receiving element in a light-dispersing including:
a first light-dispersing unit having the first light-dispersing element and a first pulse motor for driving the first light-dispersing element;
a second light-dispersing unit having the second light-dispersing element and a second pulse motor for driving the second light-dispersing element; and
a pulse transmitter for transmitting a first pulse number of pulses to the first pulse motor and a second pulse number of pulses to the second pulse motor,
wherein the first pulse number of pulses is necessary for sequentially changing, at predetermined intervals, a wavelength of monochromatic light produced by the first light-dispersing device, and
wherein the second pulse number of pulses is necessary for sequentially changing, at predetermined intervals, a wavelength of monochromatic light produced by the second light-dispersing device, and
the method comprising the steps of:
determining a transmission rate of the first pulse number of pulses based on a pulse rate within a start region, a stop region, or a slew range of the first pulse motor;
calculating a first pulse transmission time from the first pulse number of pulses and the transmission rate of the first pulse number of pulses; and
transmitting the second pulse number of pulses to the second pulse motor within the first pulse transmission time.

2. The method for synchronously driving light-dispersing elements according to claim 1, further comprising the steps of:
checking whether the transmission rate of a first portion of the second pulse number of pulses is within the start region, the stop region, or the slew range of the second pulse motor, the first portion of the second pulse number of pulses to be sent to the second pulse motor,
reducing the transmission rate of the first portion of the second pulse number of pulses while increasing the transmission rate of a second portion of the second pulse number of pulses if the transmission rate of the first portion of the second pulse number of pulses is out of the start region, the stop region, or the slew range, and
sending the second portion of the second pulse number of pulses to the second pulse motor within the first pulse transmission time.

3. A system for synchronously driving light-dispersing elements including:
a first light-dispersing unit having a first light-dispersing element and a first pulse motor for driving the first light-dispersing element; and
a second light-dispersing unit having a second light-dispersing element and a second pulse motor for driving the second light-dispersing element,
wherein the system is capable of synchronously driving the first light-dispersing element and the second light-receiving element by transmitting a first pulse number of pulses to the first pulse motor and a second pulse number of pulses to the second pulse motor,
wherein the first pulse number of pulses is necessary for sequentially changing, at predetermined intervals, a wavelength of monochromatic light produced by the first light-dispersing device, and
wherein the second pulse number of pulses is necessary for sequentially changing, at predetermined intervals, a wavelength of monochromatic light produced by the second light-dispersing device, and
the system comprising:
a) a memory section for storing synchronous drive conditions, first light-dispersing element information relating to a number of pulses to be sent to the first pulse motor and a change in the wavelength of the monochromatic light produced by the first light-dispersing element, second light-dispersing element information relating to a number of pulses to be sent to the second pulse motor and a change in the wavelength of the monochromatic light produced by the second light-dispersing element, dynamic characteristics information of the first pulse motor relating to a start region, a stop region and a slew range of the first pulse motor, and dynamic characteristics information of the second pulse motor relating to a start region, a stop region, and a slew range of the second pulse motor, wherein the synchronous drive conditions comprise a change-beginning wavelength, a change-ending wavelength, and a wavelength-change interval of the monochromatic lights produced by the first light-dispersing element and the second light-dispersing element; and
b) a pulse transmission pattern creator for creating a first pulse transmission pattern for transmitting the first pulse number of pulses to the first pulse motor within a first pulse transmission time, based on the first light-dispersing element information, a pulse rate within the start region, the stop region, or the slew range of the first pulse motor and the synchronous drive conditions, and for creating a second pulse transmission pattern for transmitting the second pulse number of pulses to the second pulse motor within the first pulse transmission time.

4. The system for synchronously driving light-dispersing elements according to claim 3,
wherein the pulse transmission pattern creator checks whether the transmission rate of a first portion of the second pulse number of pulses is within the start region, the stop region, or the slew range of the second pulse motor, the first portion of the second pulse number of pulses to be sent to the second pulse motor, and wherein if the transmission rate of the first portion of the second pulse number of pulses is out of the start region, the stop region, or the slew range, the pulse transmission pattern creator reduces the transmission rate of the first potion of the second pulse number of pulses while increasing the transmission rate of a second portion of the second pulse number of pulses, and sends the second portion of the second pulse number of pulses to the second pulse motor within the first pulse transmission time.

5. A detector for a chromatograph, comprising;

a spectrofluorometric detector; and the system for synchronously driving light-dispersing elements according to claim 3, wherein the first light dispersing unit and the second light dispersing unit are provided in and optically coupled to the spectrofluorometric detector.

6. A detector for a chromatograph, comprising;

a spectrofluorometric detector; and the system for synchronously driving light-dispersing elements according to claim 4, wherein the first light dispersing unit and the second light dispersing unit are provided in and optically coupled to the spectrofluorometric detector.

* * * * *